United States Patent [19]

Berg et al.

[11] Patent Number: 4,584,063

[45] Date of Patent: Apr. 22, 1986

[54] SEPARATION OF ACETONE FROM METHANOL BY EXTRACTIVE DISTILLATION

[76] Inventors: Lloyd Berg, 1314 S. Third Ave., Bozeman, Mont. 59715; Karl J. Warren, 2800 Sheridan Ave., Butte, Mont. 59701

[21] Appl. No.: 393,071

[22] Filed: Jun. 28, 1982

[51] Int. Cl.$^4$ ............................................. B01D 3/40
[52] U.S. Cl. ...................................... 203/51; 203/54; 203/56; 203/57; 203/60; 203/62; 203/63; 203/64; 568/411; 568/913
[58] Field of Search ....................... 203/64, 56, 51, 57, 203/60, 54, 63, 65, 62; 568/411, 413

[56] References Cited

U.S. PATENT DOCUMENTS

| | | | |
|---|---|---|---|
| 1,805,559 | 5/1931 | Barbet | 568/411 |
| 2,179,991 | 11/1939 | Bright et al. | 568/411 |
| 2,273,923 | 2/1942 | Bludworth | 203/64 |
| 3,419,477 | 12/1968 | Mattia | 568/411 |
| 3,764,627 | 10/1973 | Prinz | 568/411 |
| 4,153,516 | 5/1979 | Reed et al. | 203/64 |

FOREIGN PATENT DOCUMENTS

| | | | |
|---|---|---|---|
| 1089744 | 9/1960 | Fed. Rep. of Germany | 203/64 |
| 1142354 | 1/1963 | Fed. Rep. of Germany | 568/411 |
| 32788 | 8/1965 | German Democratic Rep. | 568/411 |

*Primary Examiner*—Wilbur Bascomb

[57] ABSTRACT

Acetone cannot be completely removed from acetone-methanol mixtures by distillation because of the presence of the minimum boiling azeotrope. Acetone can be readily separated from methanol by using extractive distillation in which the extractive agent is a higher boiling oxygenated, nitrogenous and/or sulfur-containing organic compound or a mixture of two or more of these. Typical examples of effective agents are: Glycerine, 1,5-Pentanediol, Dimethylsulfoxide, n-Hexanol, Dioctyl phthalate and N,N-Dimethylacetamide.

2 Claims, No Drawings

SEPARATION OF ACETONE FROM METHANOL BY EXTRACTIVE DISTILLATION

FIELD OF THE INVENTION

This invention relates to a method for separating acetone from methanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Acetone and methanol are two of the most widely used solvents and mixtures of these two occur with great frequency. The usual method of recovering volatile solvents is by rectification in a multiplicate column. However in this case, complete recovery by rectification is impossible due to the formation of the minimum azeotrope between these two. Acetone, b.p. 56.1° C. and methanol, b.p. 64.5° C. form a minimum azeotrope boiling at 55.7° C. at one atmosphere pressure and containing 88 weight percent acetone, 12 weight percent methanol. As pressure is increased, the azeotrope composition gets richer in methanol, thus 34% at 4.56 Atm., 46% at 7.82 Atm. and 56% at 11.6 Atm. It is therefore impossible to produce pure acetone from acetone-methanol mixtures by rectification because the lower boiling azeotrope will always come off overhead as the initial product. Any mixture of acetone and methanol subjected to rectification at one atmosphere pressure will produce an overhead product boiling at 55.7° C. and containing 88% acetone, 12% methanol.

Extractive distillation would be an attractive method of effecting the separation of acetone from methanol if agents can be found that (1) will break the acetone-methanol azeotrope and (2) are easy to recover from the methanol, that is form no azeotrope with methanol and boil sufficiently above methanol to make the separation by rectification possible with only a few theoretical plates.

Extractive distillation typically requires the addition of an equal amount to twice as much extractive agent as the acetone-methanol on each plate in the rectification column. The extractive agent should be heated to about the same temperature as the plate into which it is introduced. Thus extractive distillation imposes and additional heat requirement on the column as well as somewhat larger plates. However this is less than the increase occasioned by the additional agents required in azeotropic distillation.

Another consideration in the selection of the extractive distillation agent is its recovery in the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with methanol otherwise it will form a two phase azeotrope with the methanol in the recovery column and some other method of separation will have to be employed.

The breaking of an azeotrope by extractive distillation is a new concept. The closest application of this concept might be the breaking of the ethanol-water azeotrope. J. Schneible, U.S. Pat. No. 1,469,447 used glycerol, P. V. Smith and C. S. Carlson, U.S. Pat. No. 2,559,519 employed ethoxyethanol and butoxyethanol for this purpose and W. E. Catterall, U.S. Pat. No. 2,591,672 reported gasoline as being effective. These are dehydrations and operate more conventionally as a solvent extraction process rather than an extractive distillation

OBJECTIVE OF THE INVENTION

The object of this invention is to provide a process or method of extractive distillation that will enhance the relative volatility of acetone from methanol in their separation in a rectification column. It is a further object of this invention to identify suitable extractive distillation agents which will eliminate the acetone-methanol binary azeotrope and make possible the production of pure acetone and methanol by rectification. It is a further object of this invention to identify organic compounds which, in addition to the above constraints, are stable, can be separated from methanol by rectification with relatively few plates and can be recycled to the extractive distillation column and reused with little decomposition.

SUMMARY OF THE INVENTION

The objects of this invention are provided by a process for separating acetone from methanol which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the acetone-methanol minimum azeotrope and permit the separation of pure acetone from methanol by rectification when employed as the agent in extractive distillation. Table I lists the compounds, mixtures and approximate proportions that we have found to be exceptionally effective. Table II lists the compounds, mixtures and approximate proportions that are successful but do not give quite as high a relative volatility as that obtained from those in Table I. Table III lists those compounds and mixtures which we found to be relatively unsuccessful. The data in Tables I, II and III were obtained in a vapor-liquid equilibrium still. In each case, the starting material was the acetone-methanol azeotrope. The ratios are the parts of extractive agent used per part of acetone-methanol azeotrope. The relative volatilities are listed for each of the two ratios employed.

The compounds that are effective as extractive distillation agents when used alone are ethylene glycol, propylene glycol, 1,5-pentanediol, glycerine and dimethylsulfoxide. The compounds which are effective when used in mixtures of two or more components are diethylene glycol, triethylene glycol, hexylene glycol, dipropylene glycol, tetraethylene glycol, tripropylene glycol, 2-ethyl-1,3-hexanediol, 3-chloro-1,2-propanediol, dibutylphthalate, dioctylphthalate, diisobutylphthalate, diisooctylphthalate, butylbenzylphthalate, dimethylformamide, N,N-dimethylacetamide, isophorone, mesityl oxide, ethylene glycol diacetate, triethylene glycol diacetate, ethylacetoacetate, 4-methoxy-4-methylpentanone-2, methyl-n-propyl ketone, ethylene glycol phenyl ether, dichlorodiethyl ether, n-hexyl cellosolve, diethyl carbitol, n-butanol, n-amyl alcohol, n-hexanol, n-octanol, butoxyethanol, butoxypropanol, diacetone alcohol, cellosolve acetate and carbitol acetate.

The ratios shown in Tables I, II and III are the parts of extractive agent used per part of acetone-methanol azeotrope. The two relative volatilities correspond to the two different ratios. For example in Table I, one part of glycerine with one part of acetone-methanol azeotrope gives a relative volatility of 3.67, 6/5 parts of glycerine gives 2.92. One half part of glycerine mixed with one half part of ethylene glycol with one part of acetone-methanol azeotrope gives a relative volatility of 3.45, 3/5 parts of glycerine plus 3/5 parts of ethylene glycol gives 3.81. One third parts of glycerine plus ⅓ parts of ethylene glycol plus ⅓ parts of 1,4-butylene glycol mixed with one part of acetone-methanol azeotrope gives a relative volatility of 2.93, with 2/5 parts, these three give 3.15.

In every example in Tables I, II and III the starting material is the acetone-methanol azeotrope which possesses a relative volatility of 1.00.

Table III lists combinations of some of the same compounds presented in Tables I and II which failed to give relative volatilities as high as 2.0. It also lists some combinations that give relative volatilities of less than 1.0. This indicates the importance of employing these compounds in the proper ratio and combination.

Several of the compounds and mixtures listed in Tables I and II and whose relative volatility has been determined in the vapor-liquid equilibrium still, were then evaluated in a glass perforated plate rectification column possessing 4.5 theoretical plates. The results are listed in Table IV. The acetone-methanol azeotrope contains 88% acetone, 12% methanol. In every case the feed or bottoms composition contained less acetone than 88% and in almost every case, the overhead is richer than 88% acetone. Without the extractive agent, the overhead would be the azeotrope, 88% acetone. This proves that the extractive agent is negating the azeotrope and makes the rectification proceed as if the azeotrope no longer existed. It is our belief that this is the first time that this has been accomplished for any azeotrope. The data in Table IV was obtained in the following manner. The first line is the result obtained after one hour operation with one to two parts of extractive agent per part of acetone-methanol being boiled up to the condenser. The second line is the result after 1.5 hours which is usually the maximum time required for the equipment to come to equilibrium. Where the same extractive agent is repeated one or more times in Table IV, these indicate the runs in which the agent was recovered and recycled, this to demonstrate its stability and ability to be recycled with no adverse effect.

TABLE I

Extractive Distillation Agents Which Are Exceptionally Effective In Separating Acetone From Methanol

| Compounds | Ratios | | Relative Volatilities | |
|---|---|---|---|---|
| Glycerine | 1 | 6/5 | 3.67 | 2.92 |
| Glycerine, Ethylene glycol | $(1/2)^2$ | $(3/5)^2$ | 3.45 | 3.81 |
| Glycerine, Propylene glycol | $(1/2)^2$ | $(3/5)^2$ | 2.62 | 3.09 |
| Glycerine, 1,4-Butylene glycol | $(1/2)^2$ | $(3/5)^2$ | 2.99 | 2.83 |
| Glycerine, 1,5-Pentanediol | " | " | 2.72 | 2.96 |
| Glycerine, Dimethylsulfoxide (DMSO) | " | " | 2.73 | 2.88 |
| Ethylene glycol, DMSO | " | " | 3.53 | 3.03 |
| Glycerine, Ethylene glycol, 1,4-Butylene glycol | $(1/3)^3$ | $(2/5)^3$ | 2.93 | 3.15 |
| Glycerine, Ethylene glycol, 1,5-Pentanediol | " | " | 3.03 | 3.15 |
| Glycerine, Ethylene glycol, Diethylene glycol | " | " | 3.23 | 3.48 |
| Glycerine, Ethylene glycol, Diisobutylphthalate | " | " | 2.90 | 3.34 |
| Glycerine, DMSO, Diisooctylphthalate | " | " | 3.22 | 2.53 |
| Glycerine, DMSO, Triethylene glycol | " | " | 2.69 | 2.84 |
| Glycerine, DMSO, 1,5-Pentanediol | " | " | 2.88 | 2.87 |
| Glycerine, DMSO, 1,3-Butylene glycol | " | " | 2.75 | 2.90 |
| Glycerine, DMSO, 1,4-Butylene glycol | " | " | 3.05 | 2.98 |
| Glycerine, DMSO, Diethylene glycol | " | " | 2.96 | 3.44 |
| Dimethylsulfoxide (DMSO) | 1 | 6/5 | 3.32 | 3.18 |

TABLE II

Extractive Distillation Agents Which Are Effective In Separating Acetone From Methanol

| Compounds | Ratios | | Relative Volatilities | |
|---|---|---|---|---|
| Ethylene glycol | 1 | 6/5 | 2.48 | 3.15 |
| Propylene glycol | " | " | 2.51 | 2.30 |
| 1,3-Butylene glycol | " | " | 2.17 | 2.22 |
| 1,4-Butylene glycol | " | " | 2.47 | 2.62 |
| 1,5-Pentanediol | " | " | 2.15 | 2.63 |
| Ethylene glycol, Propylene glycol | $(1/2)^2$ | $(3/5)^2$ | 2.44 | 2.65 |
| Ethylene glycol, 1,4-Butylene glycol | " | " | 2.40 | 2.78 |
| Ethylene glycol, 1,5-Pentanediol | " | " | 2.64 | 2.62 |
| Ethylene glycol, Diethylene glycol | " | " | 2.67 | 2.70 |
| Glycerine, Diethylene glycol | " | " | 2.52 | 2.62 |
| Glycerine, 1,5-Pentanediol | " | " | 2.71 | 2.79 |
| Glycerine, Hexylene glycol | " | " | 2.49 | 2.53 |
| Glycerine, Diisobutylphthalate | " | " | 1.88 | 2.35 |
| Glycerine, Diisooctylphthalate | " | " | 2.24 | 2.58 |
| Glycerine, Dioctylphthalate | " | " | 1.93 | 2.33 |
| Glycerine, N,N—Dimethylacetamide | " | " | 2.38 | 2.36 |
| Diethylene glycol, 1,5-Pentanediol | " | " | 2.56 | 2.41 |
| Glycerine, 1,3-Butylene glycol | " | " | 2.57 | 2.29 |
| Dimethylsulfoxide (DMSO), | $(1/2)^2$ | $(3/5)^2$ | 2.29 | 2.71 |

TABLE II-continued

Extractive Distillation Agents Which Are Effective In Separating Acetone From Methanol

| Compounds | Ratios | | Relative Volatilities | |
|---|---|---|---|---|
| Propylene glycol | | | | |
| DMSO, Hexylene glycol | " | " | 2.27 | 2.18 |
| DMSO, Diethylene glycol | " | " | 2.49 | 1.66 |
| DMSO, Dipropylene glycol | " | " | 2.23 | 2.26 |
| DMSO, Ethylene glycol diacetate | " | " | 2.02 | 2.08 |
| DMSO, Triethylene glycol diacetate | " | " | 2.05 | 2.25 |
| DMSO, Dioctylphthalate | " | " | 2.05 | 2.05 |
| DMSO, Diisodecylphthalate | " | " | 2.16 | 2.07 |
| DMSO, Ethylacetoacetate | " | " | 1.95 | 2.07 |
| DMSO, Mesityl oxide | " | " | 2.30 | 2.12 |
| DMSO, 4-Methoxy-4-methyl-pentanone-2 | " | " | 1.89 | 2.24 |
| DMSO, Methyl-n-propyl ketone | " | " | 2.13 | 2.16 |
| DMSO, Isophorone | " | " | 2.15 | 2.15 |
| DMSO, Ethylene glycol phenyl ether | " | " | 2.11 | 1.97 |
| DMSO, Dichlorodiethyl ether | " | " | 2.07 | 2.00 |
| Glycerine, Ethylene glycol, Dipropylene glycol | $(1/3)^3$ | $(2/5)^3$ | 2.40 | 2.57 |
| Glycerine, Ethylene glycol, 1,3-Butylene glycol | " | " | 2.59 | 2.77 |
| Glycerine, Ethylene glycol, Hexylene glycol | " | " | 2.31 | 2.72 |
| Glycerine, Ethylene glycol, 3-Chloro-1,2-propanediol | " | " | 2.19 | 2.18 |
| Glycerine, Ethylene glycol, n-Hexyl Cellosolve | " | " | 1.99 | 2.06 |
| Glycerine, Ethylene glycol, Diethyl Carbitol | " | " | 2.36 | 2.10 |
| Glycerine, Ethylene glycol, Triethylene glycol | " | " | 2.71 | 2.89 |
| Glycerine, Ethylene glycol, Tetraethylene glycol | " | " | 2.70 | 2.95 |
| Glycerine, Ethylene glycol, Dibutylphthalate | " | " | 2.38 | 3.10 |
| Glycerine, Ethylene glycol, Dioctylphthalate | " | " | 2.50 | 3.36 |
| Glycerine, Ethylene glycol, Diisooctylphthalate | " | " | 2.33 | 2.39 |
| Glycerine, Ethylene glycol, Diisodecylphthalate | " | " | 2.85 | 3.09 |
| Glycerine, Ethylene glycol, n-Butanol | " | " | 2.38 | 2.15 |
| Glycerine, Ethylene glycol, n-Hexanol | " | " | 2.48 | 2.28 |
| Glycerine, Ethylene glycol, n-Octanol | " | " | 2.28 | 2.93 |
| Glycerine, Ethylene glycol, Butoxyethanol | " | " | 2.40 | 2.62 |
| Glycerine, Ethylene glycol, Butoxypropanol | " | " | 2.85 | 2.40 |
| Glycerine, Ethylene glycol, Diacetone alcohol | " | " | 2.16 | 1.96 |
| Glycerene, Ethylene glycol, Ethylene glycol phenyl ether | " | " | 2.62 | 2.77 |
| Glycerine, Ethylene glycol, Dipropylene glycol methyl ether | " | " | 2.55 | 2.21 |
| Glycerine, Ethylene glycol, Cellosolve acetate | " | " | 2.38 | 2.22 |
| Glycerine, Ethylene glycol, Carbitol acetate | " | " | 2.10 | 2.55 |
| Glycerine, Ethylene glycol, Dimethylformamide | " | " | 2.31 | 2.26 |
| Glycerine, Ethylene glycol, Propylene glycol | " | " | 2.56 | 2.62 |
| Glycerine, Propylene glycol, Dimethylformamide | " | " | 2.08 | 2.03 |
| Glycerine, DMSO, Ethylene glycol | " | " | 2.59 | 2.82 |
| Glycerine DMSO, Propylene glycol | " | " | 2.46 | 2.63 |
| Glycerine, DMSO, Hexylene glycol | $(1/3)^3$ | $(2/5)^3$ | 2.16 | 2.43 |
| Glycerine, DMSO, Diethylene glycol | " | " | 2.36 | 2.71 |
| Glycerine, DMSO, Dipropylene glycol | " | " | 2.73 | 2.51 |
| Glycerine, DMSO, Tripropylene glycol | " | " | 2.86 | 2.58 |
| Glycerine, DMSO, Tetraethylene glycol | " | " | 2.31 | 2.54 |
| Glycerine, DMSO, 2-Ethyl-1,3-hexanediol | " | " | 2.34 | 2.28 |
| Glycerine, DMSO, 3-Chloro-1,2-propanediol | " | " | 1.88 | 2.64 |
| Glycerine, DMSO, Butoxpropanol | " | " | 1.99 | 2.08 |
| Glycerine, DMSO, Dibutyl-phthalate | " | " | 2.13 | 1.95 |
| Glycerine, DMSO, Diisobutyl-phthalate | " | " | 1.83 | 2.96 |
| Glycerine, DMSO, Dioctyl-phthalate | " | " | 2.57 | 2.77 |
| Glycerine, DMSO, Diisodecyl-phthalate | " | " | 2.54 | 2.48 |
| Glycerine, DMSO, Ethylene glycol phenyl ether | " | " | 2.24 | 2.13 |
| Glycerine, 1,4-Butylene glycol, Diisooctylphthalate | " | " | 2.03 | 2.33 |

TABLE III

Extractive Distillation Agents Which Are Relatively Ineffective In Separating Acetone From Methanol

| Compounds | Ratios | | Relative Volatilities | |
|---|---|---|---|---|
| Dimethylformamide | 1 | 6/5 | 1.64 | 1.36 |
| Diacetamide | " | | 1.07 | |
| Ethylacetoacetate | " | | 0.43 | |
| Isophorone | " | | 0.89 | |
| Mesityl oxide | " | " | 0.59 | 0.64 |
| Diethylene glycol | " | " | 1.67 | 1.72 |
| Methyl n-propyl ketone | " | " | 0.79 | 0.71 |
| 4-Methoxy-4-methylpentanone-2 | " | " | 1.21 | 1.42 |
| Diisobutyl ketone | " | " | 0.79 | 0.86 |
| Hydroquinone, Acetophenone | $(1/2)^2$ | $(3/5)^2$ | 1.03 | — |
| Catechol, Acetophenone | " | | 1.01 | |
| DMSO, Dimethylformamide | " | | 1.94 | |
| DMSO, Ethylacetoacetate | " | | 1.95 | |
| Dimethylformamide, Ethylacetoacetate | " | | 1.48 | |
| DMSO, Acetophenone | " | " | 1.70 | 1.86 |
| Dimethylformamide, Acetophenone | " | | 1.29 | |
| Ethylacetoacetate, Acetophenone | " | | 0.56 | |
| DMSO, Benzophenone | " | " | 1.88 | 2.03 |
| Dimethylformamide, Isophorone | " | | 0.76 | |
| Dimethylformamide, 2,4-Pentanedione | " | | 1.06 | |
| DMSO, Diacetone alcohol | " | | 1.95 | |
| Acetophenone | 1 | | 0.65 | |
| DMSO, Phorone | $(1/2)^2$ | $(3/5)^2$ | 1. | |
| Dimethylformamide, Mesityl oxide | " | | 1.20 | |
| DMSO, 2,4-Pentanedione | " | " | 1.76 | 1.82 |
| DMSO, Dichlorodiethyl ether | " | " | 2.07 | 2.00 |
| DMSO, Diethylene glycol dimethyl ether | " | | 1.99 | |
| DMSO, Ethylbutyl ketone | " | " | 1.62 | 2.56 |
| Dimethylformamide, Ethylbutyl ketone | " | " | 2.29 | 2.37 |
| DMSO, Dioxan | " | " | 1.71 | 1.57 |
| DMSO, Methylisobutyl ketone | " | " | 1.56 | 1.50 |
| DMSO, Methyl n-amyl ketone | " | " | 1.28 | 1.30 |
| DMSO, Methyl isoamyl ketone | " | " | 1.54 | 1.40 |
| Dimethylformamide, Diisobutyl ketone | " | " | 1.16 | 0.76 |
| DMSO, 2-Octanone | " | " | 1.06 | 0.90 |
| Dimethylformamide, 4-Methoxy-4-methylpentanone-2 | " | " | 1.60 | 1.86 |
| Ethylbutyl ketone, 4-Methoxy-4-methylpentanone-2 | " | " | 1.74 | 1.76 |
| Diisobutyl ketone, 4-Methoxy-4-methylpentanone-2 | " | " | 1.33 | 1.42 |
| DMSO, Cellosolve acetate | " | " | 1.98 | 1.89 |
| Dimethylformamide, Cellosolve | " | " | 1.28 | 1.28 |

TABLE III-continued

Extractive Distillation Agents Which Are Relatively Ineffective In Separating Acetone From Methanol

| Compounds | Ratios | | Relative Volatilities | |
|---|---|---|---|---|
| acetate | | | | |
| Ethylene glycol diacetate, Cellosolve acetate | " | " | 0.86 | 0.80 |
| DMSO, Acetylsalicylic acid | " | " | 1.67 | 1.72 |
| Dimethylformamide, Acetophenone | " | " | 1.14 | 1.10 |
| Dimethylformamide, Acetylsalicyclic acid | " | " | 1.15 | 1.07 |
| Dimethylformamide, Glycerol triacetate | " | " | 1.37 | 1.46 |
| DMSO, Butoxypropanol | " | " | 2.10 | 1.85 |
| Dimethylformamide, Butoxypropanol | " | " | 1.47 | 1.41 |
| Ethylene glycol phenyl ether, Butoxypropanol | " | " | 1.19 | 1.12 |
| Dimethylformamide, Diethylene glycol | " | " | 1.86 | 1.85 |
| DMSO, Diisooctylphthalate | " | " | 2.00 | 1.92 |
| Dimethylformamide, Diisooctylphthalate | " | " | 1.41 | 1.25 |
| DMSO, Glycerol triacetate | " | " | 1.78 | 1.91 |
| DMSO, Methyl n-propyl ketone | " | " | 1.73 | 1.62 |
| Dimethylformamide, Methyl n-propyl ketone | " | " | 1.25 | 1.50 |
| Dimethylformamide, Dioctylphthalate | " | " | 1.12 | 1.27 |
| Dimethylformamide, Dipropylene glycol methyl ether | " | " | 1.53 | 2.08 |
| DMSO, Dipropylene glycol methyl methyl | " | " | 1.47 | 1.37 |
| Diethylene glycol, Dioctylphthalate | " | " | 1.46 | 1.38 |
| Diethylene glycol, Diisooctylphthalate | " | " | 1.28 | 1.29 |
| DMSO, Dibutylphthalate | " | " | 1.82 | 2.00 |
| Glycerine, Dimethylformamide | " | " | 1.96 | 1.99 |
| Glycerine, Hexylene glycol diacetate | " | " | 2.01 | 1.49 |
| Glycerine, Triethylene glycol diacetate | " | " | 2.09 | 1.92 |
| Glycerine, Adiponitrile | $(1/2)^2$ | $(3/5)^2$ | 1.64 | 1.38 |
| Glycerine, Butoxypropanol | " | " | 2.08 | 1.82 |
| Ethylene glycol, Diisooctylphthalate | " | " | 1.89 | 1.98 |
| Glycerine, DMSO, 1,4-Pentanedione | $(1/3)^3$ | $(2/5)^3$ | 1.33 | 1.71 |
| Glycerine, DMSO, Dioctylphthalate (2-phase) | " | " | 2.21 | 2.64 |
| Glycerine, Dimethylformamide, Diisobutylphthalate | " | " | 1.65 | 1.50 |
| Glycerine, Dimethylformamide, Dioctylphthalate | " | " | 1.76 | 1.72 |
| Glycerine, Dimethylformamide, Diisodecylphthalate | " | " | 1.73 | 1.89 |
| Glycerine, Ethylene glycol, Ethylacetoacetate | " | " | 2.02 | 1.92 |
| Resorcinol, Phenol, Acetophenone | " | " | 0.63 | 0.78 |
| Hydroquinone, Phenol, Acetophenone | " | " | 0.64 | 0.53 |
| Catechol, Phenol, Acetophenone | " | " | 0.90 | 0.73 |
| Resorcinol, Phenol, Ethylacetoacetate | " | " | 0.61 | 0.70 |
| Hydroquinone, Phenol, Ethylacetoacetate | " | " | 0.64 | 0.64 |
| Catechol, Phenol, Ethylacetoacetate | " | " | 0.74 | 0.65 |
| Resorcinol, Phenol, Dimethylformamide | " | " | 0.71 | 0.66 |
| Catechol, Hydroquinone, Acetophenone | " | " | 1.21 | 1.19 |
| Resorcinol, Phenol, Dimethylformamide | " | | 1.16 | |
| Hydroquinone, Acetophenone | $(1/2)^2$ | | 1.03 | |
| Catechol, Acetophenone | " | | 1.01 | |
| DMSO, Dimethylformamide | " | | 1.94 | |
| Hydroquinone, Resorcinol, Ethylacetoacetate, Dimethylformamide | $(1/4)^4$ | $(3/10)^4$ | 0.66 | 1.01 |

TABLE IV

Data From Runs Made in Rectification Column

| Extractive Agent(s) | Overhead-% Acetone | Bottoms-% Acetone | Relative Volatility |
|---|---|---|---|
| DMSO | 99.2 | 15 | 4.35 |
| " | 99.4 | 15 | 4.55 |
| DMSO | 98.9 | 15 | 3.99 |
| " | 96.0 | 15 | 2.98 |
| DMSO | 99.7 | 25 | 4.59 |
| " | 99.9 | 25 | 5.92 |
| DMSO | 87.6 | 15 | 2.27 |
| " | 92.9 | 15 | 2.60 |
| Dimethylformamide (DMFA) | 70.8 | 15 | 1.79 |
| " | 73.8 | 15 | 1.85 |
| DMFA | 81.5 | 50 | 1.39 |
| " | 92.4 | 50 | 1.74 |
| 50% DMFA, 50% Diethylene glycol | 98.5 | 50 | 2.54 |
| " | 97.1 | 50 | 2.19 |
| 50% DMFA, 50% Diethylene glycol | 94.2 | 30 | 2.24 |
| " | 93.7 | 30 | 2.20 |
| 50% DMSO, 50% Cellosolve acetate | 90.0 | 50 | 1.63 |
| " | 94.8 | 50 | 1.91 |
| 50% DMSO, 50% Cellosolve acetate | 85.8 | 50 | 1.49 |
| " | 84.6 | 50 | 1.46 |
| 50% DMSO, 50% Cellosolve acetate | 86.5 | 50 | 1.51 |
| " | 86.8 | 50 | 1.52 |
| 50% DMSO, Butoxypropanol | 99.0 | 50 | 2.78 |
| " | 100.0 | 50 | — |
| 50% DMSO, Butoxypropanol | 84.1 | 15 | 2.13 |
| " | 83.6 | 15 | 2.11 |
| 50% DMSO, 50% Glycerine | 99.7 | 50 | 3.64 |
| " | 99.8 | 50 | 4.13 |
| 50% DMSO, 50% Glycerine | 90.0 | 25 | 2.08 |
| " | 90.6 | 25 | 2.11 |
| Propylene glycol | 96.8 | 50 | 2.13 |
| " | 99.2 | 50 | 2.90 |
| Propylene glycol | 98.1 | 25 | 3.07 |

TABLE IV-continued
Data From Runs Made in Rectification Column

| Extractive Agent(s) | Overhead-% Acetone | Bottoms-% Acetone | Relative Volatility |
|---|---|---|---|
| 33% Glycerine, 33% Ethylene glycol, 33% DMSO | 89.5 | 50 | 1.61 |
| " | 93.5 | 50 | 1.81 |
| 33% Glycerine, 33% Ethylene glycol, 33% DMSO | 88.3 | 30 | 1.89 |
| " | 89.9 | 30 | 1.96 |
| 50% DMSO, 50% Propylene glycol | 98.4 | 50 | 2.51 |
| " | 99.1 | 50 | 2.82 |
| 50% DMSO, 50% Propylene glycol | 96.5 | 25 | 2.67 |
| " | 96.8 | 25 | 2.73 |
| 50% Glycerine, 50% Ethylene glycol | 100 | 50 | — |
| " | 100 | 50 | — |
| 50% Glycerine, 50% Ethylene glycol | 95.7 | 25 | 2.54 |
| " | 97.2 | 25 | 2.81 |
| 50% DMSO, 50% Ethylene glycol | 100 | 50 | — |
| " | 100 | 50 | — |
| 50% DMSO, 50% Ethylene glycol | 97.8 | 25 | 2.98 |
| " | 97.9 | 25 | 2.99 |
| 33% Glycerine, 33% Ethylene glycol, 33% Diethylene glycol | 98.4 | 50 | 2.55 |
| " | 98.4 | 50 | 2.50 |
| 33% Glycerine, 33% Ethylene glycol, 33% Diethylene glycol | 96.9 | 25 | 2.74 |
| " | 96.7 | 25 | 2.71 |
| 33% Glycerine, 33% Ethylene glycol, 33% 1,5-Pentanediol | 97.9 | 50 | 2.35 |
| " | 99.2 | 50 | 2.92 |
| 33% Glycerine, 33% Ethylene glycol, 33% Triethylene glycol | 99.3 | 50 | 3.00 |
| " | 99.6 | 50 | 3.51 |
| 33% Glycerine, 33% Ethylene glycol, 33% Triethylene glycol | 98.9 | 25 | 3.46 |
| " | 97.2 | 25 | 2.81 |
| 50% Glycerine, 50% Propylene glycol | 96.4 | 50 | 2.07 |
| " | 99.7 | 50 | 3.67 |
| 50% Ethylene glycol, 50% 1,5-Pentanediol | 99.3 | 25 | 3.86 |
| " | 98.6 | 25 | 3.28 |
| 1,5-Pentanediol | 93.6 | 25 | 2.32 |
| " | 96.4 | 25 | 2.65 |
| 1,4-Butanediol | 96.7 | 25 | 2.71 |
| " | 96.8 | 25 | 2.72 |
| 50% Glycerine, 33% Ethylene glycol, 17% Propylene glycol | 94.5 | 25 | 2.40 |
| " | 94.1 | 25 | 2.36 |

THE USEFULNESS OF THE INVENTION

The usefulness or utility of this invention can be demonstrated by referring to the data presented in Tables I, II and IV. All of the successful extractive distillation agents show that acetone can be removed from its binary minimum azeotrope with methanol by means of distillation in a rectification column and that the ease of separation as measured by relative volatility is considerable. Without these extractive distillation agents, no improvement above the azeotrope composition will occur in the rectification column. The data also show that the most attractive agents will operate at a boiling rate low enough to make this a useful and efficient method of recovering high purity acetone from any mixture with methanol including the minimum azeotrope. The stability of the compounds used and the boiling point difference is such that complete recovery and recycle is obtainable by a simple distillation and the amount required for make-up is small.

WORKING EXAMPLES

Example 1

The acetone-methanol azeotrope is 88% acetone, 12% methanol. Fifty grams of the acetone-methanol azeotrope and fifty grams of ethylene glycol were charged to an Othmer type glass vapor-liquid equilibrium still and refluxed for eleven hours. Analysis of the vapor and liquid by gas chromatography gave vapor 91.9% acetone, 8.1% methanol; liquid of 80.9% acetone, 19.1% methanol. This indicates a relative volatility of 2.48. Ten grams of ethylene glycol were added and refluxing continued for another thirteen hours. Analysis indicated a vapor composition of 91.6% acetone, 8.4% methanol, a liquid composition of 77.7% acetone, 22.3% methanol which is a relative volatility of 3.15.

Example 2

Fifty grams of acetone-methanol azeotrope, 25 grams of ethylene glycol and 25 grams of glycerine were charged to the vapor-liquid equilibrium still and refluxed for seventeen hours. Analysis indicated a vapor composition of 92.4% acetone, 7.6% methanol, a liquid composition of 77.9% acetone, 22.1% methanol which is a relative volatility of 3.45. Five grams of ethylene glycol and five grams of glycerine were added and refluxing continued for another ten hours. Analysis indicated a vapor composition of 92.3% acetone, 7.7% methanol, a liquid composition of 75.8% acetone, 24.2% methanol which is a relative volatility of 3.81.

Example 3

Fifty grams of the acetone-methanol azeotrope, 25 grams of ethylene glycol and 25 grams of dimethylsulfoxide were charged to the vapor-liquid equilibrium still and refluxed for eleven hours. Analysis indicated a vapor composition of 91.9% acetone, 8.1% methanol, a liquid composition of 76.3% acetone, 23.7% methanol which is a relative volatility of 3.53. Five grams of ethylene glycol and five grams of dimethylsulfoxide were added and refluxing continued for another twelve hours. Analysis indicated a vapor composition of 91.1% acetone, 8.9% methanol, a liquid composition of 77.1% acetone, 22.9% methanol which is a relative volatility of 3.03.

Example 4

A glass perforated plate rectification column was calibrated with ethylbenzene and p-xylene which possesses a relative volatility of 1.06 and found to have 4.5 theoretical plates. A solution of 375 grams of methanol and 125 grams of acetone was placed in the stillpot and heated. When refluxing began, an extractive agent containing 50% ethylene glycol and 50% glycerine was pumped into the column at a rate of 22–23 ml./min. The temperature of the extractive agent as it entered the column was 46° C. After establishing the feed rate of the extractive agent, the temperature of the acetone and methanol in the stillpot was adjusted to give a total reflux rate of 10–20 ml./min. After one hour of operation, overhead and bottoms samples of approximately two ml. were collected and analysed using gas chromatography. The overhead analysis was 95.7% acetone and 4.3% methanol. The bottoms analysis was 25% acetone and 75% methanol. Using these compositions in the Fenske equation, with the number of theoretical plates in the column being 4.5, gave an average relative volatility of 2.54 for each theoretical plate. After 1.5 hours of total operating time, the overhead and bottoms samples were again taken and analysed. The overhead composition was 97.2% acetone and 2.8% methanol and the bottoms composition was 25% acetone and 75% methanol. This gave an average relative volatility of 2.81 for each theoretical plate.

Example 5

A solution of 375 grams of methanol and 125 grams of acetone was placed in the stillpot of the same column used in Example 4 and heat applied. When refluxing began an extractive agent of 50% dimethylsulfoxide and 50% ethylene glycol was fed into the top of the column at a feed rate of 22–23 ml./min. and a temperature of 46° C. After establishing the feed rate of the extractive agent, the temperature of the acetone and methanol in the stillpot was adjusted to give a total reflux rate of 10–20 ml./min. Having established the reflux rate, the column was allowed to operate for one hour. After one hour of steady operation, overhead and bottoms samples of approximately two ml. were collected and analysed using gas chromatography. The overhead analysis was 97.8% acetone and 2.3% methanol. The bottoms analysis was 25% acetone and 75% methanol. Using these compositions in the Fenske equation with the number of theoretical plates of the column being 4.5, gave an average relative volatility of 2.98 for each theoretical plate. After 1.5 hours of total operation, the overhead composition was 97.9% acetone and 2.1% methanol and the bottoms composition was 25% acetone and 75% methanol. This gave an average relative volatility of 2.99 for each theoretical plate.

We have shown that by the use of the proper compound or combination of compounds as agents, acetone can be effectively removed from its mixture with methanol in any proportion including the minimum azeotrope.

The nature of the present invention having been described, what we wish to claim as new and useful and secure by Letters Patent is:

1. A method for recovering acetone from a mixture of acetone and methanol which comprises distilling a mixture of acetone and methanol in a rectification column in the presence of about one to two parts of extractive agent per part of acetone-methanol mixture, recovering essentially pure acetone as overhead product and obtaining the extractive agent and methanol from the stillpot or reboiler, the extractive agent comprises at least dimethylsulfoxide.

2. The method of claim 1 in which the extractive agent comprises dimethylsulfoxide and at least one material from the group consisting of ethylene glycol, glycerine, triethylene glycol, 1,5-pentanediol, 1,3-butanediol, 1,4-butanediol, diethylene glycol, propylene glycol, hexylene glycol, isophorone, dipropylene glycol, polyethylene glycol, ethylene glycol diacetate, triethylene glycol diacetate, dioctyl phthalate, mesityl oxide, 4-methoxy-4-methylpentanone-2, ethylene glycol phenyl ether, tripropylene glycol, tetraethylene glycol, 2-ethyl-1,3-hexanediol, diisodecyl phthalate and ethylene glycol ethyl ether acetate.

* * * * *